United States Patent
Soliz et al.

(10) Patent No.: US 9,925,519 B1
(45) Date of Patent: Mar. 27, 2018

(54) COMPOSITION OF MAGNETIC MATERIALS FOR SENSING AND DECONTAMINATING TOXIC CHEMICALS

(71) Applicant: U.S. Army Edgewood Chemical Biological Center, APG, MD (US)

(72) Inventors: Jennifer R Soliz, Baltimore, MD (US); Christopher J Karwacki, Churchville, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 15/710,272

(22) Filed: Sep. 20, 2017

Related U.S. Application Data

(62) Division of application No. 15/179,076, filed on Jun. 10, 2016, now Pat. No. 9,770,703.

(60) Provisional application No. 62/174,738, filed on Jun. 12, 2015.

(51) Int. Cl.
| | |
|---|---|
| *B01D 53/04* | (2006.01) |
| *B01J 20/28* | (2006.01) |
| *A62D 3/33* | (2007.01) |
| *G01N 21/35* | (2014.01) |
| *G01N 21/33* | (2006.01) |
| *G01N 21/65* | (2006.01) |
| *G01N 27/72* | (2006.01) |
| *B01J 20/06* | (2006.01) |
| *C01G 49/00* | (2006.01) |
| *A62D 101/02* | (2007.01) |

(52) U.S. Cl.
CPC .......... *B01J 20/28009* (2013.01); *A62D 3/33* (2013.01); *B01D 53/04* (2013.01); *B01J 20/06* (2013.01); *C01G 49/0054* (2013.01); *G01N 21/33* (2013.01); *G01N 21/35* (2013.01); *G01N 21/65* (2013.01); *G01N 27/72* (2013.01); *A62D 2101/02* (2013.01); *B01D 2253/1124* (2013.01); *B01D 2257/204* (2013.01); *B01D 2257/2064* (2013.01); *B01D 2257/2066* (2013.01); *B01D 2257/302* (2013.01); *B01D 2257/304* (2013.01); *B01D 2257/306* (2013.01); *B01D 2257/70* (2013.01); *B01D 2259/4583* (2013.01); *C01P 2006/42* (2013.01)

(58) Field of Classification Search
CPC . B01D 53/04; A62D 3/33; B01J 20/06; C01G 49/0054; G01N 21/33
USPC ......................................... 588/315
See application file for complete search history.

(56) References Cited

U.S. PATENT DOCUMENTS 9,770,703 B1 * 9/2017 Soliz .................. B01J 20/28009

* cited by examiner

*Primary Examiner* — Edward Johnson
(74) *Attorney, Agent, or Firm* — Ulysses John Biffoni

(57) ABSTRACT

A method and composition of matter for detecting and decontaminating hazardous chemicals, the composition of matter including: a magnetic material for any of chemisorbing, molecularly dissociating, or decomposing a hazardous chemical, wherein the magnetic material changes its magnetic moment upon any of chemisorption, decomposition, and molecular dissociation of the hazardous chemical and the change in magnetic moment is used to detect the presence of the hazardous chemical, and wherein the hazardous chemical includes any of toxic industrial chemicals, chemical warfare agents, and chemical warfare agent related compounds.

5 Claims, 13 Drawing Sheets

COMPOSITION OF MAGNETIC MATERIALS FOR SENSING AND DECONTAMINATING TOXIC CHEMICALS

CROSS-REFERENCE TO RELATED APPLICATIONS

This application is a divisional of application Ser. No. 15/179,076 filed on Jun. 10, 2016, now U.S. Pat. No. 9,770,703, which is commonly assigned. This application also claims the benefit of U.S. Provisional Application No. 62/174,738, filed on Jun. 12, 2015 and entitled "Magnetic Materials for Sensing and Decontaminating Toxic Chemicals," the complete disclosure of which, in its entirety, is hereby incorporated by reference.

GOVERNMENT INTEREST

The embodiments described herein may be manufactured, used, and licensed by or for the United States Government.

BACKGROUND

Technical Field

The embodiments herein relate to sensing and decontaminating toxic chemicals, and more particularly to using a magnetic material for sensing and decontaminating toxic chemicals.

Description of the Related Art

Magnetic nanoparticles are attractive materials owing to their wide range in applications, e.g. chemical sensors, biomedical diagnostics, magnetic resonance imaging, drug delivery, catalysis, memory data storage, and multiferroics. Some of the desirable features nanoparticles have to offer are (1) controlled and finite sizes, (2) large surface area to volume ratios, (3) tailored surface functionalities, and (4) thermally robust crystalline structures.

SUMMARY

In view of the foregoing, an embodiment herein provides a composition of matter comprising: a magnetic material for any of chemisorbing, molecular dissociating, and decomposing a hazardous chemical, wherein the magnetic material undergoes a change in magnetic moment upon any of chemisorption, decomposition, and molecular dissociation of the hazardous chemical, and wherein the hazardous chemical comprises any of chemical warfare agent and chemical warfare agent related compounds.

The change in magnetic moment may stem from a change in a cation valency upon any of the chemisorption, decomposition, and molecular dissociation of the hazardous chemical. The composition of matter may further comprise a material that shows change in any of IR spectra, UV-Vis spectra, Raman spectra, and impedance spectra, wherein the change correlates to the any of chemisorption, decomposition, and molecular dissociation of the hazardous chemical, and wherein the change in impedance spectra results from an electronic property change in the material upon the any of chemisorption, decomposition, and molecular dissociation of the hazardous chemical.

The magnetic material may comprise a $Fe_2O_3$ polymorph that performs any of chemisorbing, decomposing, and molecular dissociating the hazardous chemical. The magnetic material may comprise a $LnFe_2O_4$ compound, where Ln is a lanthanide that performs any of chemisorbing, decomposing, and molecular dissociating the hazardous chemical. The magnetic material may comprise salts of various metals, wherein the metal salt compound performs any of chemisorbing, decomposing, and molecular dissociating the hazardous chemical.

The metal salt compound may comprise: any of iron I, iron II, iron III, and iron IV as cations; and any of oxide, chloride, sulfide, sulfate, sulfite, fluoride, nitride, nitrate, oxynitride, and oxyfluoride as anions. The metal salt compound may comprise any of iron I hydroxide, iron II hydroxide, iron III hydroxide, and iron IV hydroxide. The metal salt compound may comprise any of lanthanide oxide and lanthanide iron oxide. The metal salt compound may comprise any of manganese II oxide, manganese III oxide, and manganese IV oxide.

The metal salt compound may comprise manganese tetraoxide. The metal salt compound may comprise: any of manganese II, manganese III, and manganese IV as cations; and any of oxide, chloride, sulfide, sulfate, sulfite, fluoride, nitride, nitrate, oxynitride, and oxyfluoride as anions. The metal salt compound may comprise any of cobalt II oxide and cobalt III oxide. The metal salt compound may comprise cobalt as cation, and any of oxide, chloride, sulfide, sulfate, sulfite, fluoride, nitride, nitrate, oxynitride, and oxyfluoride as anions. The metal salt compound may comprise any of nickel II oxide, and nickel III oxide.

The metal salt compound may comprise any of copper I oxide, and copper II oxide. The metal salt compound may comprise copper II hydroxide. The metal salt compound may comprise: copper II as cation; and any of oxide, chloride, sulfide, sulfate, sulfite, fluoride, nitride, nitrate, oxynitride, and oxyfluoride as anion.

An embodiment herein provides a method comprising: providing a magnetic material; exposing the magnetic material to a hazardous chemical; and detecting the hazardous chemical using a change in a magnetic moment of the magnetic material in accordance with the chemical exposure, wherein the change in the magnetic moment stems from a change in a cation valency of the magnetic material upon any of chemisorption, decomposition, and molecular dissociation with the hazardous chemical, and wherein the hazardous chemical comprises any of toxic industrial chemicals, chemical warfare agents, chemical warfare agent related compounds.

The detecting may further comprise using a change in any of IR spectra, UV-Vis spectra, Raman spectra, and impedance spectra of the magnetic material upon any of chemisorption, decomposition, and molecular dissociation with the hazardous chemical, and wherein the change in impedance spectra results from an electronic property change in the material upon the any of chemisorption, decomposition, and molecular dissociation of the hazardous chemical. The hazardous chemical may comprise any of G, V, and H class chemical warfare agents. The hazardous chemical may comprise any of sulfur mustard (HD), VX, VE, VG, VM, VR, tabun (GA), soman (GD), cyclosarin (GF), and sarin (GB).

The hazardous chemical may comprise chemical warfare agent structural analogs, wherein the chemical comprises any of 2-chloroethyl ethyl sulfide (2-CEES), 2-chloroethylmethyl sulfide (CEMS), dimethyl methylphosphonate (DMMP), dimethyl chlorophosphate (DMCP), diisopropyl methylphosphonate (DIMP), methyl dichlorophosphate (MDCP), diethyl methanephosphonate, diethyl ethanephosphonate, 2,4-dichlorophenol, triethyl phosphate, and diisopropyl fluorophosphonate (DFP). The hazardous chemical may comprise any of acidic or basic gases and vapors. The hazardous chemical may comprise any of ammonia, hydrogen chloride, sulfur dioxide, hydrogen sulfide, and cyanogen chloride. The method may further comprise integrating the magnetic material into a wearable chemical sensor.

An embodiment herein provides a device comprising a substrate supporting a magnetic material fabricated as a thin film on the substrate; a circuit board, wherein the substrate is placed on the circuit board; a rare-Earth magnet connected to the circuit board; an inductor capacitor (LC) circuit detector connected to the circuit board, wherein the LC circuit is configured to measure a change in a signal from the thin film upon any of chemisorption, decomposition, and molecular dissociation with a hazardous chemical, causing a change in magnetic moment in the magnetic material, and wherein the hazardous chemical comprises any of a toxic industrial compound, chemical warfare agent, and chemical warfare agent related compounds.

The device may further comprise: a source and a detector equipped with a fiber optic cable and configured to monitor the any of chemisorption, decomposition, and molecular dissociation of the hazardous chemical, wherein the source comprises any of an infrared (IR) source, an ultraviolet visible (UV-Vis) source, and a Raman source, and wherein the detector comprises any of an IR detector, an UV-Vis detector, and a Raman detector. The rare Earth magnet, the LC, the IR source, the IR detector, the UV-Vis source, the UV-Vis detector, the Raman source, and the Raman detector may be configured to measure a toxic analyte of interest of the hazardous chemical.

The magnetic material may be configured to provide changes in a field comprising any of a magnetic moment, an IR spectrum, a UV-Vis spectrum, and Raman spectrum. The magnetic material may be fabricated upon the substrate configured to provide any of colorimetric response upon sensitivity and reactivity with the toxic analyte of interest. The fiber optic cable may be configured to provide optical transport from measurements collected via any of the IR, UV-Vis, and Raman spectra.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION

Figure 1A:
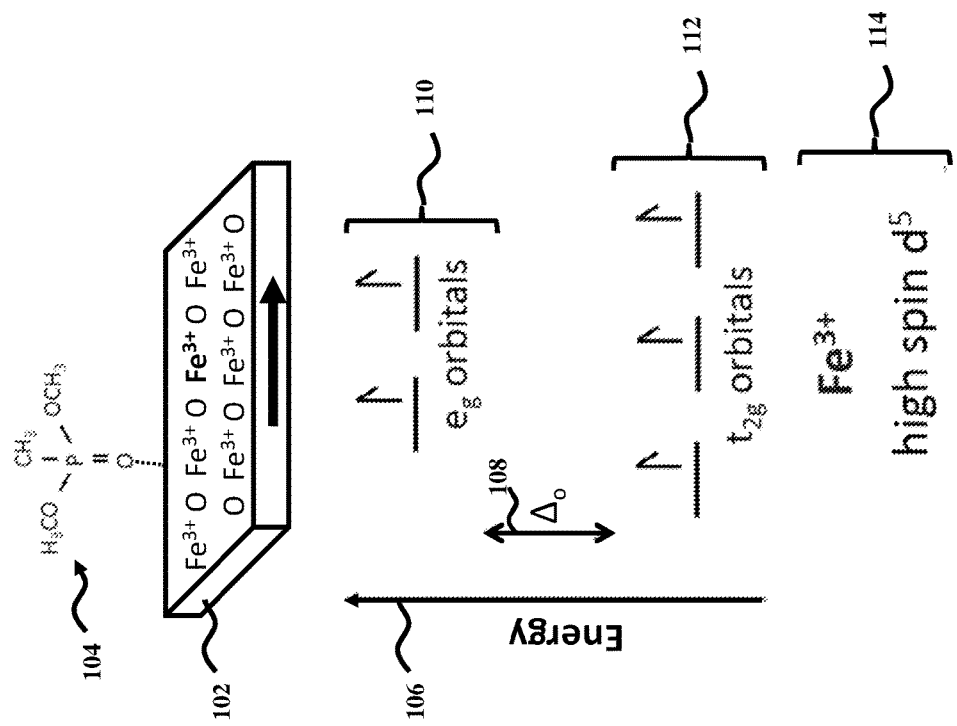
FIG. 1A is a schematic diagram illustrating a material undergoing adsorption according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide magnetic materials for reacting with, sensing, and decontaminating toxic chemicals. Magnetic materials exhibit attractive features that allow the embodiments herein to be utilized in many applications, in particular use as hazardous chemical sensors.

One material that has shown promise for any of chemisorption, molecular dissociation, and sensing of chemical warfare agent (CWA) structural analogs is $Fe_2O_3$. This compound is desirable as opposed to non-transition metal oxides for many reasons. $Fe_2O_5$ (1) shows sensitivity to various hazardous chemicals, correlating to changes in the cation valency upon chemisorption, (2) exhibits ferrimagnetic ordering with a net magnetic moment of 2.5 n/f.u., (3) has a high Neel temperature, (4) is a semi-conductor, (5) is cost effective, and (6) is chemically stable. Compounds exhibiting examples of these properties are helpful to integrate into suitable devices for hazardous chemical detection and/or decontamination. Other materials that may be synthesized and explored for sensing CWA structural analogs are $LnFe_2O_4$ (Ln=lanthanides), wherein the lanthanide may be selected from the group consisting of Ce, Pr, Nd, Pm, Eu, and Tb, and in particular $TmFe_2O_4$. Not only does $TmFe_2O_4$ exhibit ferrimagnetic ordering, but it also manifests semi-conducting behavior and sensitivity to various hazardous chemicals. The embodiments herein describe ferrite based compounds as they show promise toward sensing and removal of CWA structural analogs.

$Fe_2O_3$ and $LnFe_2O_4$ compounds are environmentally friendly, non-hazardous magnetic materials useful for chemically interacting with toxic chemicals, CWA structural analogs and related compounds.

The embodiments herein describe a composition of $Fe_2O_3$ polymorphs and $LnFe_2O_4$ materials. The magnetic materials described herein utilize binary and ternary metal oxides, such as $Fe_2O_3$ and $LnFe_2O_4$, and are applicable to a wider range of magnetic materials that can chemisorb and react with hazardous chemicals.

The embodiments herein further describe magnetic materials, specifically magnetic metal oxides (including hydroxides), and even more specifically $Fe_2O_3$ polymorphs and novel $LnFe_2O_4$ materials, for reacting with, sensing, and removal of hazardous chemicals and CWA structural analogs. Upon chemisorption of these hazardous chemicals, the magnetic materials decompose the aforementioned chemicals and can be used to sense or detect hazardous chemicals by spectral changes from multiple techniques. Such techniques include, but are not limited to, infrared spectroscopy and magnetometry. Other techniques may also be used, such as UV-Vis spectroscopy, Raman spectroscopy, and impedance spectroscopy. This type of multifunctional chemical detection may be applicable to several fields, including sensing, decontamination, separations, catalysis, and others. In particular, the embodiments described herein can be utilized in applications involving hazardous chemical detection, and potentially for use as multifunctional chemical sensors for toxic chemicals, CWA structural analogs and related compounds.

The embodiments herein provide for synthesizing $LnFe_2O_4$ compounds. The conventional approaches do not generally describe synthesizing $LnFe_2O_4$ compounds; but, synthesizing these compositions are important. The embodiments herein also indicate that $LnFe_2O_4$ compounds are reactive and can remove CWA structural analogs and related compounds.

Referring now to the drawings, and more particularly to FIGS. 1A through 5, where similar reference characters denote corresponding features consistently throughout the figures, there are shown preferred embodiments.

FIG. 1A is a schematic diagram illustrating an adsorbent magnetic material 102 according to an embodiment herein. In an embodiment, dimethyl methylphosphonate (DMMP) 104 is adsorbed to the surface of material 102. Shown below material 102 is the crystal field splitting 108 with energy 106 as the y-axis for the d-orbitals 110 and 112 of high spin $Fe^{3+}$ 114.

Figure 1B:
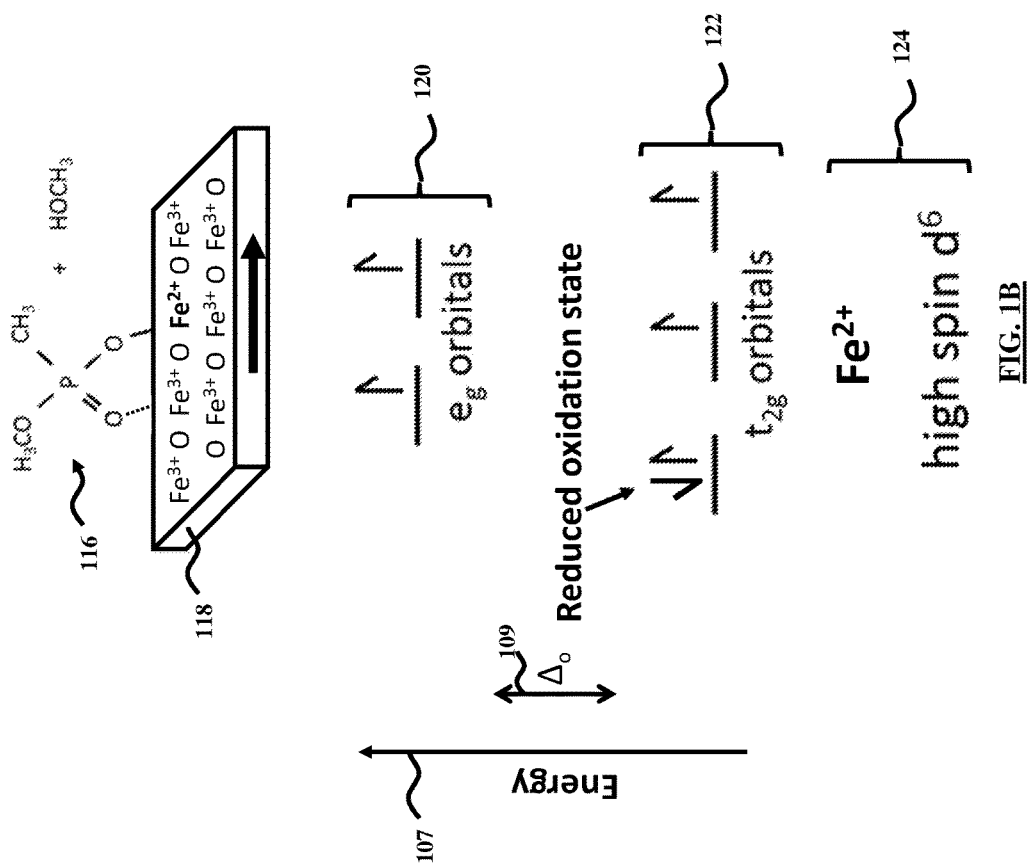
FIG. 1B is a schematic diagram illustrating a molecular dissociation of a hazardous chemical and a material undergoing a change in its oxidation state, according to an embodiment herein.

FIG. 1B, with reference to FIG. 1A, is a schematic diagram illustrating the molecular dissociation of a bound hazardous chemical 116 causing a change in the iron cation valency from the adsorbent material 18 comprising $Fe_2O_3$. Shown below material 118 is the crystal field splitting 109 with energy 107 as the y-axis for the d-orbitals 120 and 122 of high spin $Fe^2$ 124. As the hazardous chemical 116 is adsorbed to the surface of material 118, the chemical 116 undergoes molecular dissociation; thereby causing reduction of $Fe^{3+}$ to $Fe^{2+}$ 124 as shown by the added electron (bolded electron spin pointing down) in the $t_{2g}$ orbitals 122. FIG. 1B illustrates DMMP 116 bound to $Fe_2O_3$ 118, which correlates to a change in the iron cation valency. To further analyze this phenomenon found in $Fe_2O_3$ and $LnFe_2O_4$ compounds, two methods are used to study (1) the change in the magnetic moment with an applied magnetic field, and (2) the chemical interactions between the organophosphonate compounds and materials of interest via infrared spectroscopy. This qualitative and quantitative change in the cation valency is an indication that the material has decontaminated the CWA(s), i.e., meaning CWA structural analogs are present, and therefore acts as a chemical sensor as well. This may be useful in multiple applications. For example, the material can be developed into a device for hazardous chemical sensing, used as a decontaminant material integrated into wipes or sprayable slurry, or fabricated onto a cloth fabric material to be used as a wearable chemical sensor.

Adsorbent material 102 and $LnFe_2O_3$ are also photoactive, which can be made use as photoelectrodes or applied toward photocatalysis or photoelectrochemical applications. These materials are also n-type semiconductors, which can have charge carrier transport applications. Exhibiting these properties could lead to other relevant sensing applications for CWA structural analogs and related compounds. In some embodiments, certain magnetic materials may change color upon chemisorption with hazardous chemicals; thus paving the road for self-indicating colorimetric response applications or other multifunctional applications.

The chemistry of CWAs with different materials can vary; however, reactions of interest relevant to these technologies are stoichiometric reactions, resulting in cation valency reduction from the transition metal oxides. Similar reactions also occur with other CWA structural analogs. Thus, these oxides can react and remove CWA structural analogs and related compounds.

The embodiments herein describe a composition that adsorbs, reacts with, and decontaminates CWA structural analogs and related compounds, correlating to a change in the magnetic moment and the presence of the phosphonate stretch from organophosphonate species.

Figure 2A:
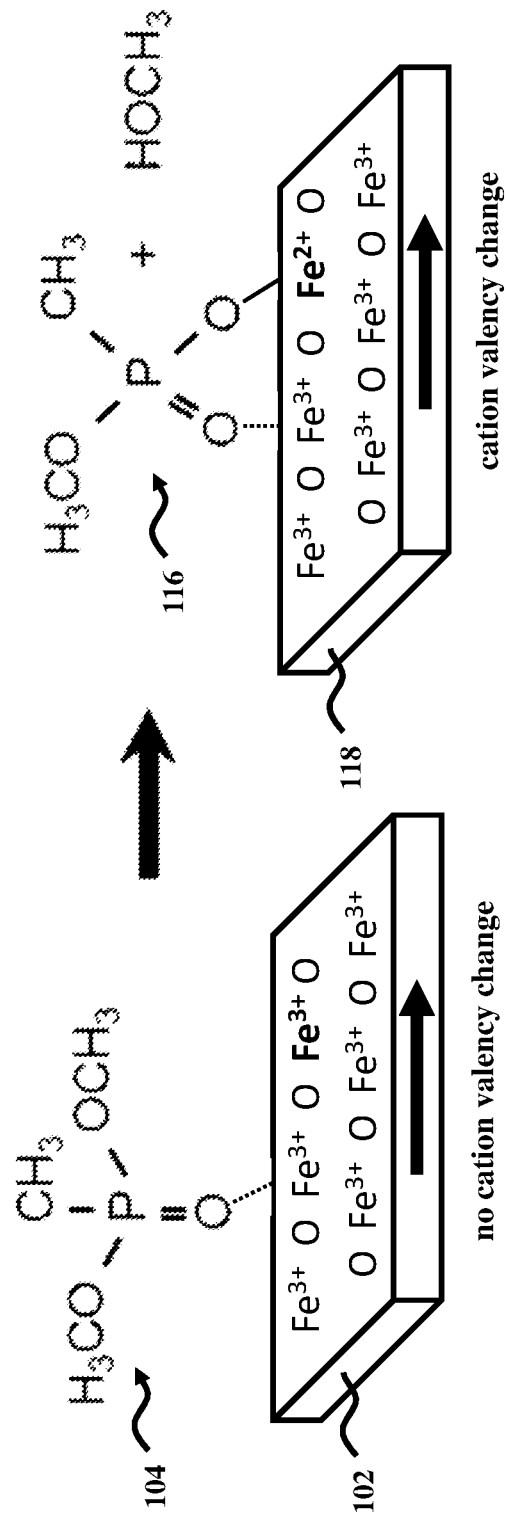
FIG. 2A is a schematic diagram illustrating a reaction according to an embodiment herein.

FIG. 2A, with reference to FIGS. 1A and 1B, is a schematic diagram of a test experiment illustrating reactivity with CWA structural analogs, according to an embodiment herein. In the exemplary test embodiment of FIG. 2A, DMMP 104 is first adsorbed to $Fe_2O_3$ 102 and then undergoes molecular dissociation. As shown on the right side of FIG. 2A, the resulting chemical species 116 is bound to the surface of material 118; thereby resulting in a reduction of the cations in material 118. The formation of cyanide, halide, or methoxy species from oxidation of G-series nerve agents or related compounds are one reactive pathway. Some embodiments herein may use detection of thiols associated with VX or other V-agents. Several magnetic materials of interest include, but are not limited to, $Fe_2O_3$ or $TmFe_2O_4$. The compositions provided in the embodiments herein include $LnFe_2O_4$, $Fe_2O_3$ polymorphs, and other magnetic materials.

Figure 2B:
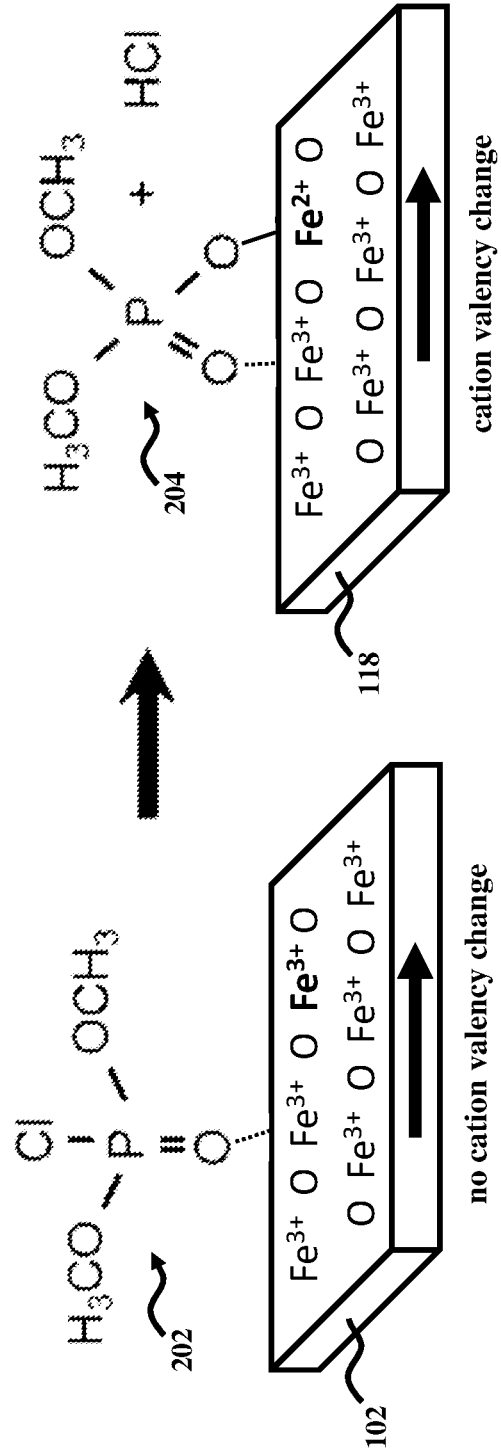
FIG. 2B is a schematic diagram illustrating a reaction according to an embodiment herein.

FIG. 2B, with reference to FIGS. 1A through 2A, is a schematic diagram of a test experiment illustrating the adsorbent material 102 exposed to dimethyl chlorophosphate (DMCP) 202. As DMCP 202 is adsorbed to the surface of material 102, DMCP 202 undergoes molecular dissociation, resulting in a surface bound chemical species 204 to material 118 and a reduction in cation valency in material 118. In some exemplary embodiments herein, polymorphs of $Fe_2O_3$ have been dosed with a variety of hazardous chemicals or CWA structural analogs, which have shown infrared spectral variance (adsorption and molecular dissociation of CWA structural analogs) and changes to the magnetic moments from $Fe_2O_3$ 118 as well as other metal-oxides (including metal-hydroxides).

Figure 2C:
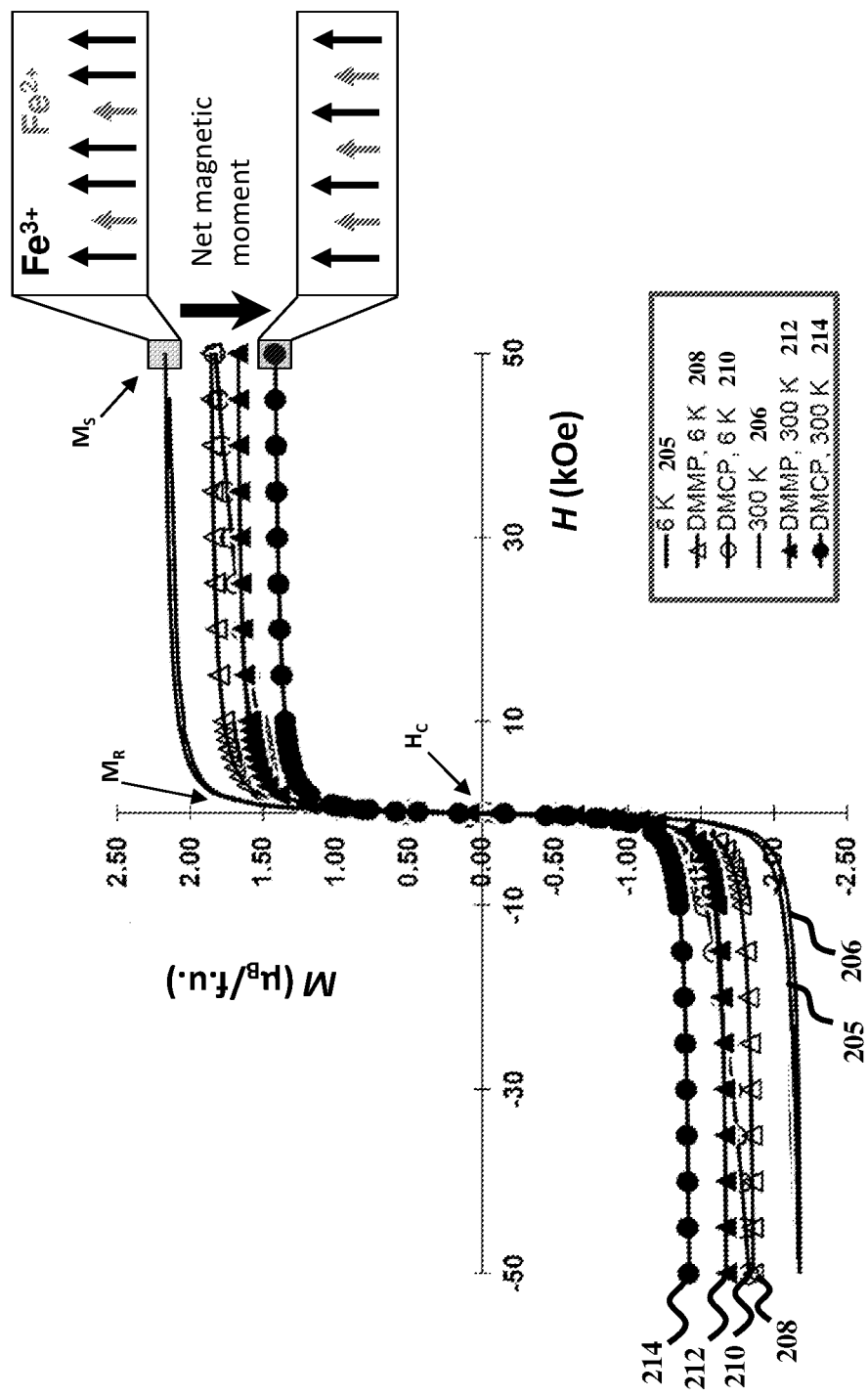
FIG. 2C is a diagram illustrating test results according to an embodiment herein.

FIG. 2C, with reference to FIGS. 1A through 2B, is a diagram illustrating test results according to an embodiment herein. Using an applied magnetic field of 50 kOe, magnetic hysteresis loops, which are a measure of the magnetization (M) as a function of the applied magnetic field strength (H), were collected prior to chemical exposures to $Fe_2O_3$ 102 at 6 K (line 205) and 300 K (line 206). FIG. 2C, for example, illustrates the change in saturated magnetization (Ms), remanent magnetization (MR), and coercivity (He) of $Fe_2O_3$ 102 with chemical exposures to DMMP 104 and DMCP 202 at 6 K and 300 K. The 6 K magnetization (line 208) decreases when exposed to DMMP 104 by 14%, and the 6 K magnetization (line 210) decreases as well when exposed to DMCP 202 by 15%. The room temperature magnetization (line 212) of $Fe_2O_3$ 102 is decreased by 23% when exposed to DMMP 104, and the room temperature magnetization (line 214) of $Fe_2O_3$ 102 is decreased by 35% when exposed to DMCP 202.

Figure 2D:
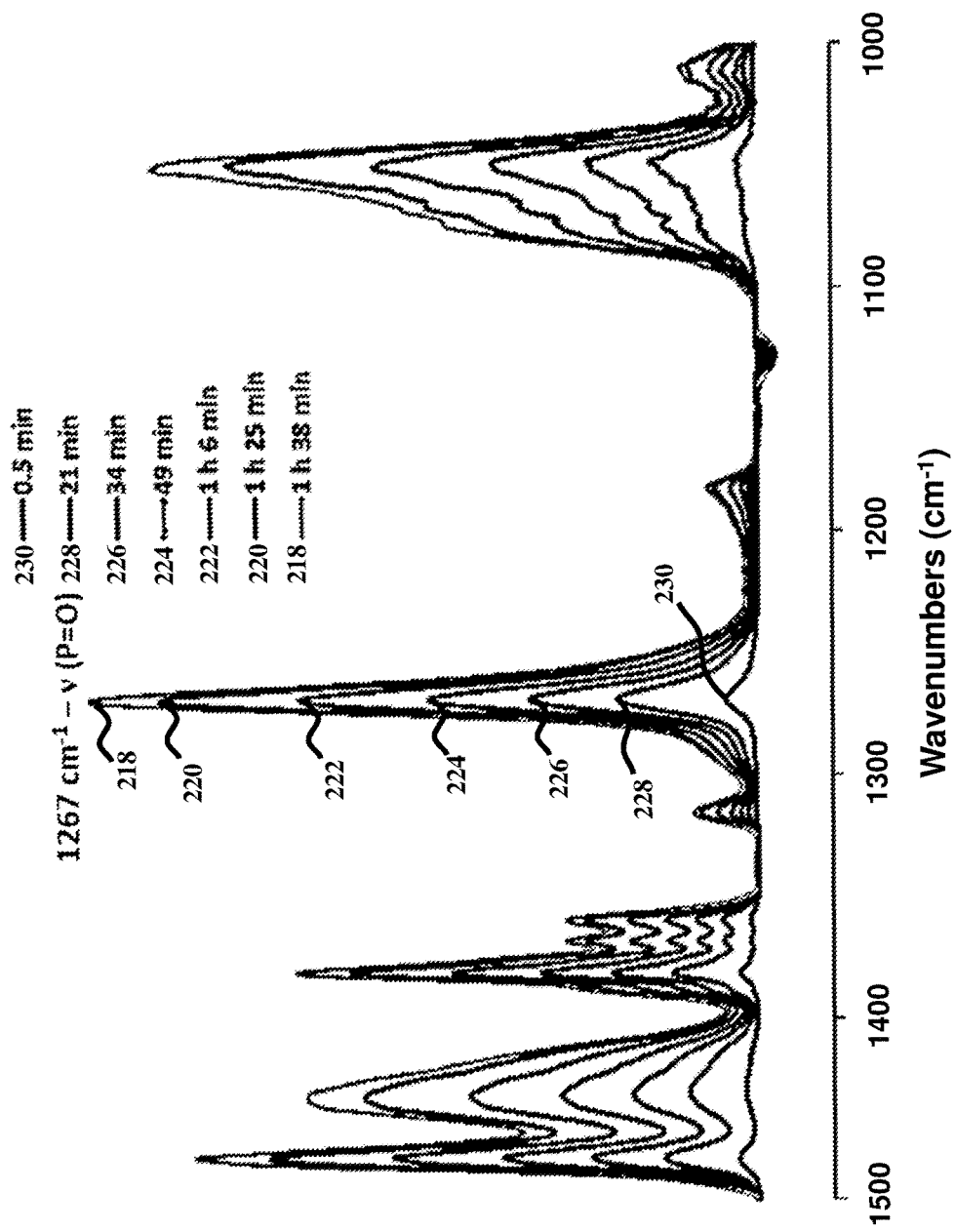
FIG. 2D is a diagram illustrating test results according to an embodiment herein.
Figure 2E:
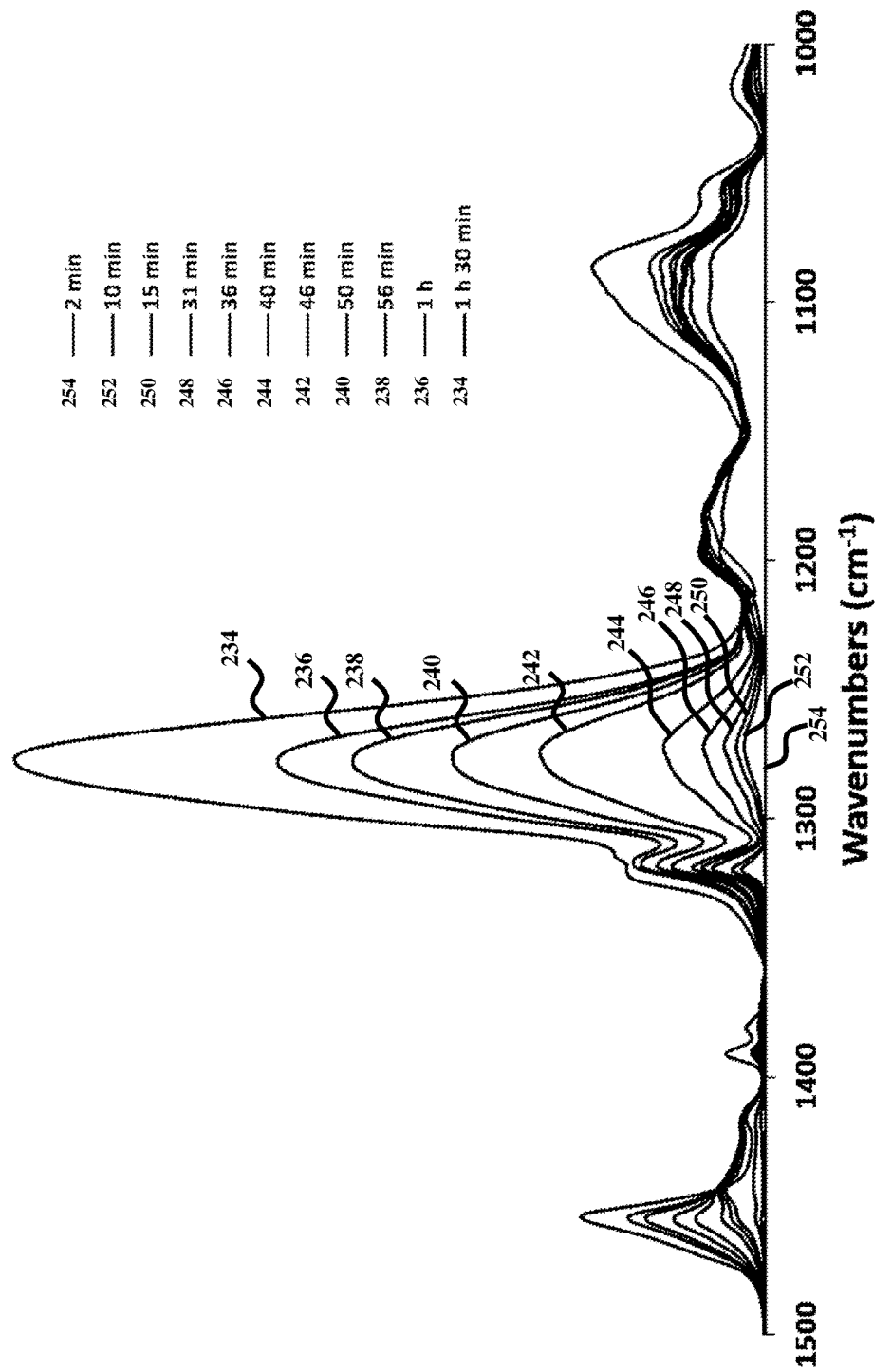
FIG. 2E is a diagram illustrating test results according to an embodiment herein.
Figure 2F:
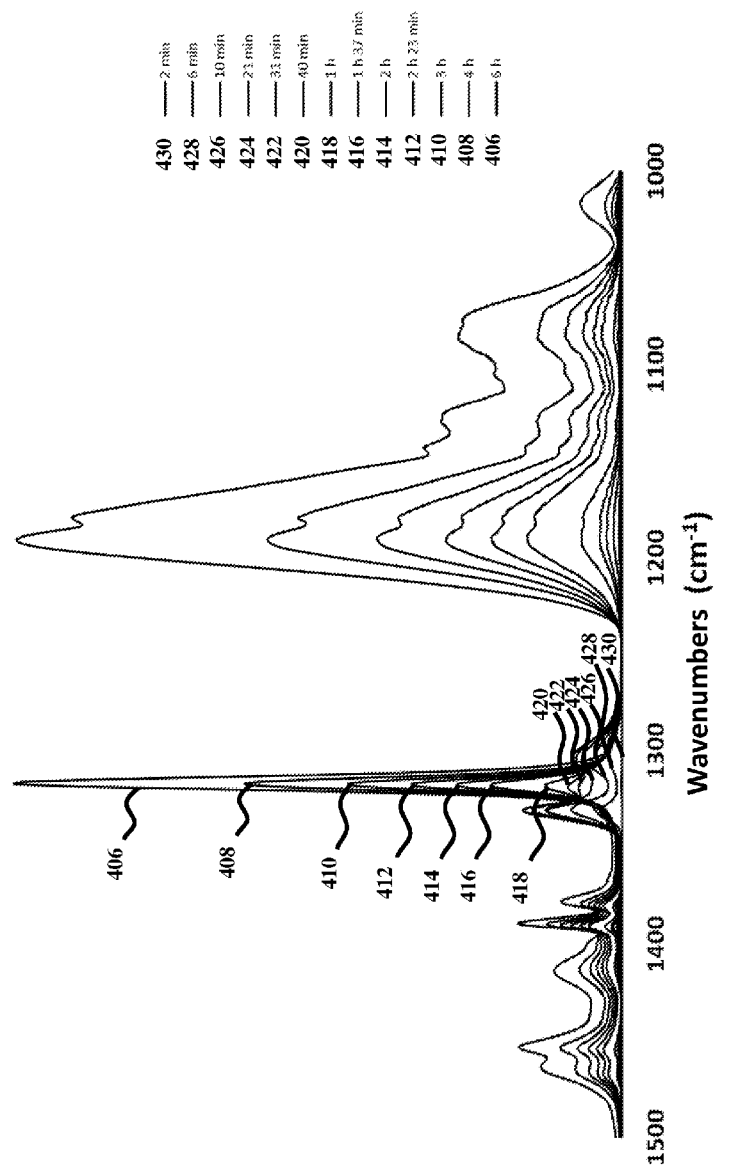
FIG. 2F is a diagram illustrating test results according to an embodiment herein.

FIGS. 2D, 2E, and 2F, with reference to FIGS. 1A through 2C, illustrates results of test experiments according to embodiments herein. In exemplary embodiments, infrared spectroscopy results show the vibrational phosphonate stretch along with other relevant vibrational modes present from the adsorption and/or molecular dissociation of DMMP 104, DMCP 202, and tabun (GA) exposures on $Fe_2O_3$ 102. As shown in FIG. 2D, the in-situ infrared spectra are timed measurements, i.e. 0.5 min (line 230), 21 min (line 228), 34 min (line 226), 49 min (line 224), 1 h 6 min (line 222), 1 h 25 min (line 220), and 1 h 38 min (line 218), collected as $Fe_2O_3$ 102 is continually exposed to DMMP 104. FIG. 2E shows the in-situ infrared spectra of $Fe_2O_3$ 102 as the material was exposed to DMCP 202, according to an exemplary embodiment. 2 min (line 254), 10 min (line 252), 15 min (line 250), 31 min (line 248), 36 min (line 246), 40 min (line 244), 46 min (line 242), 50 min (line 240), 56 min (line 238), 1 h (line 236), and 1 h 30 min (line 234) are timed in-situ infrared measurements collected on $Fe_2O_3$ 102 as the material was exposed to DMCP 202. FIG. 2F shows the in-situ infrared spectra collected on $Fe_2O_3$ 102 as the material was exposed to tabun agent, according to an exemplary embodiment. 2 min (line 430), 6 min (line 428), 10 min (line 426), 21 min (line 424), 31 min (line 422), 40 min (line 420), 1 h (line 418), 1 h 37 min (line 416), 2 h (line 414), 2 h 23 min (line 412), 3 h (line 410), 4 h (line 408), and 6 h (line 406) are timed in-situ infrared measurements collected on $Fe_2O_3$ 102 as the material was exposed to tabun agent. The cyanide and phosphonate stretches from tabun exposure was observed on $Fe_2O_3$ 102. Coupling these two techniques to observe these changes would be one method to fully capture a comprehensive understanding of this phenomenon. Other techniques such as X-Ray photoelectron spectroscopy have confirmed the presence of the chloride and phosphorus peaks from in situ exposure of DMCP 202 on $Fe_2O_3$ 102 in addition to a change in the cation valency. Thus, the method described herein captures an understanding of how $Fe_2O_3$ 102 and other similar magnetic materials can be used as chemical sensors and decontaminants for CWA structural analogs and related compounds.

As these materials have shown sensitivity toward CWA structural analogs, an embodiment herein provides coupling two or more techniques as an approach to use these compounds for multifunctional chemical sensing applications.

Figure 3A:
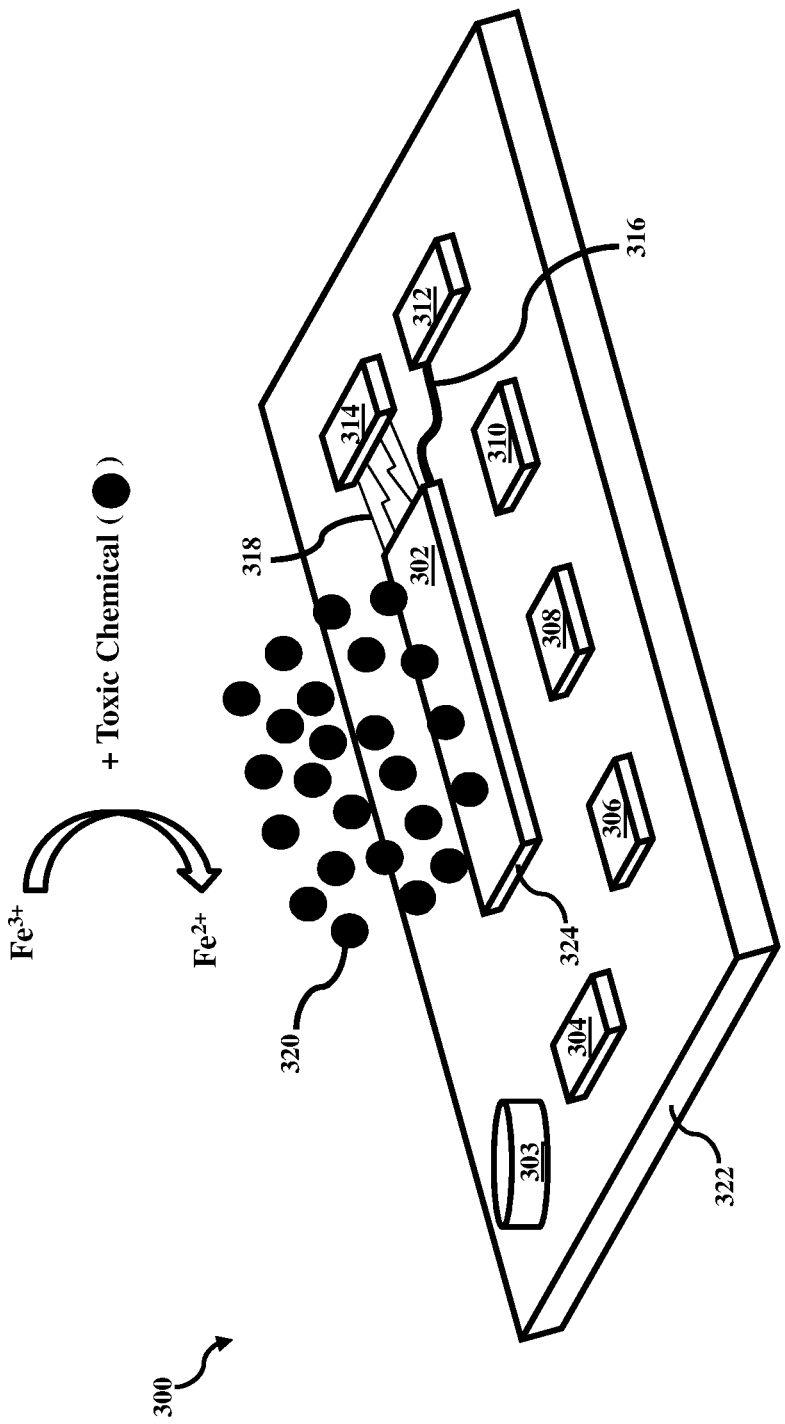
FIG. 3A is a schematic diagram illustrating a system for sensing a toxic chemical according to an embodiment herein.

FIG. 3A, with reference to FIGS. 1A through 2F, is a schematic diagram illustrating the adsorbent magnetic material 302 fabricated on a suitable substrate 324, which is supported on a circuit board 322. In an embodiment, the magnetic material 302 is configured to provide changes in a field, including any of a magnetic moment, an IR spectrum, a UV-Vis spectrum, and a Raman spectrum. In an embodiment, the magnetic material 302 is configured to provide a colorimetric response upon sensitivity and/or reactivity with a toxic analyte of interest 320. In an embodiment, the substrate 324 is used as a support for the magnetic material 302. This heterostructure can be used as a multifunctional chemical sensor for an analyte 320 of interest in the presence of a magnetic field, infrared source (or other sources, e.g. UV-Visible source, Raman source), and suitable detectors. FIG. 3A illustrates sensing device 300 that includes the use of a small rare-Earth magnet 303 and LC circuit detector 314 equipped with connectors 318 to provide the applied magnetic field and to monitor changes in signal, respectively. This type of detector can be coupled with a source 304 and a photoconductive detector 312 connected to a fiber optic cable 316; thereby obtaining ex situ or in situ spectra. The source 304 may be any of an IR source, a UV-Vis source, and a Raman source, and the detector 314 may be any of an IR detector, a UV-Vis detector, and a Raman detector. In an embodiment, the fiber optic cable 316 is configured to provide an optical transport for measurements collected from the IR, UV-Vis, or Raman spectroscopies. This can confirm the presence and identify CWA structural analogs and/or related analytes 320. Other techniques may also be used, e.g., impedance spectroscopy. Thus, coupling these two techniques with the magnetic material of interest 302 can provide multifunctional chemical detection for CWA structural analogs, stemming from the variance in magnetic moment and spectral changes. For ease of data storage and transfer, a SD memory card 308 and USB port 310 are included on the circuit board 322 as well as a lithium ion battery 306 to be able to recharge the device 300.

Figure 3B:
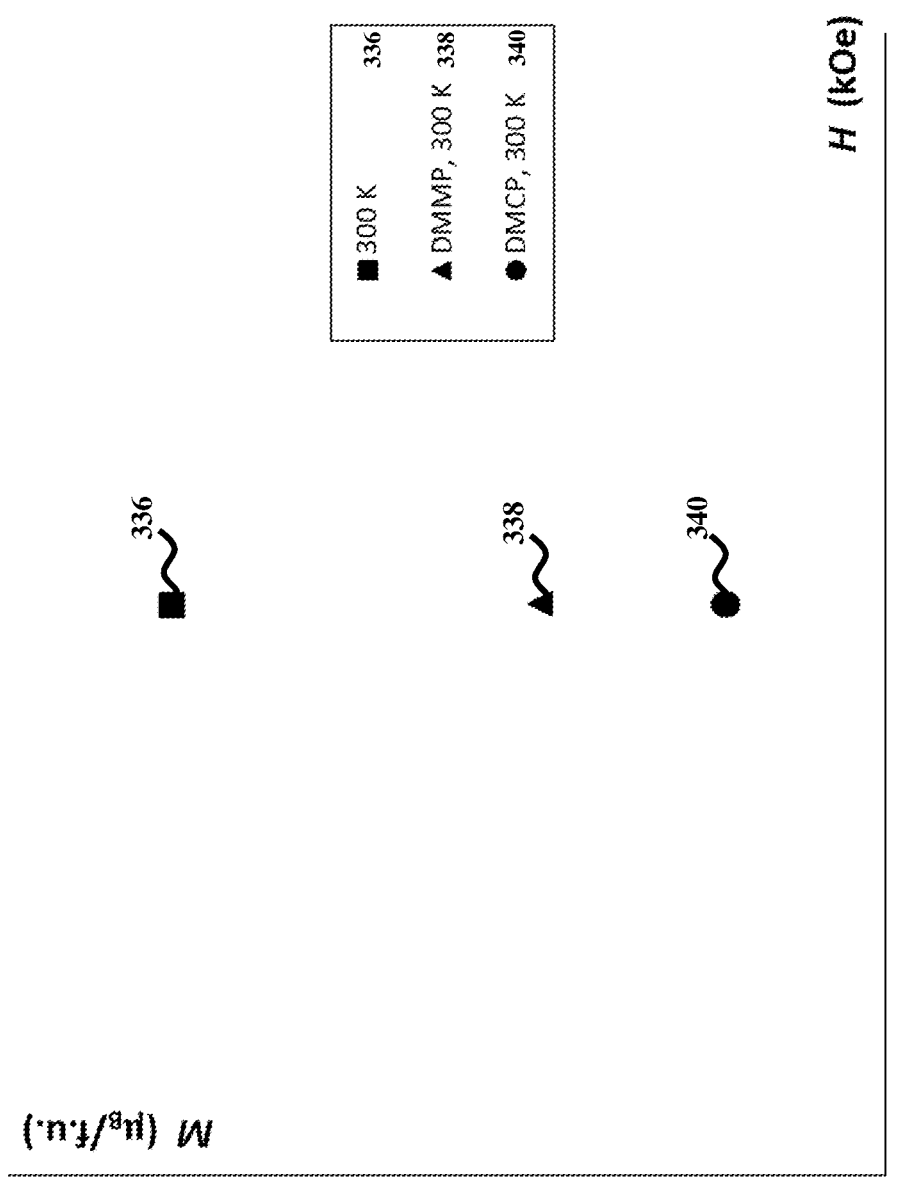
FIG. 3B is a diagram illustrating test results according to an embodiment herein.

FIG. 3B, with reference to FIGS. 1A through 3A, is a diagram illustrating test results of room temperature magnetic moments of a material of interest 302 from device 300, according to an embodiment herein. When using a cooling and/or heating system with the device 300, the magnetizations from the magnetic material of interest 302 can be accrued as well; thus varying the temperature can impact the magnetic results obtained. Using the applied magnetic field of magnet 303 from the device 300, the change in magnetization (M) can be measured as a function of applied magnetic field strength (H), as shown in FIG. 3B. The magnetization 336 was measured for $Fe_2O_3$ 102 at 300 K prior to chemical exposure. The magnetization 338 of $Fe_2O_3$ 102 decreased when exposed to DMMP 104, and the magnetization 340 decreased when exposed to DMCP 202.

Figure 3C:
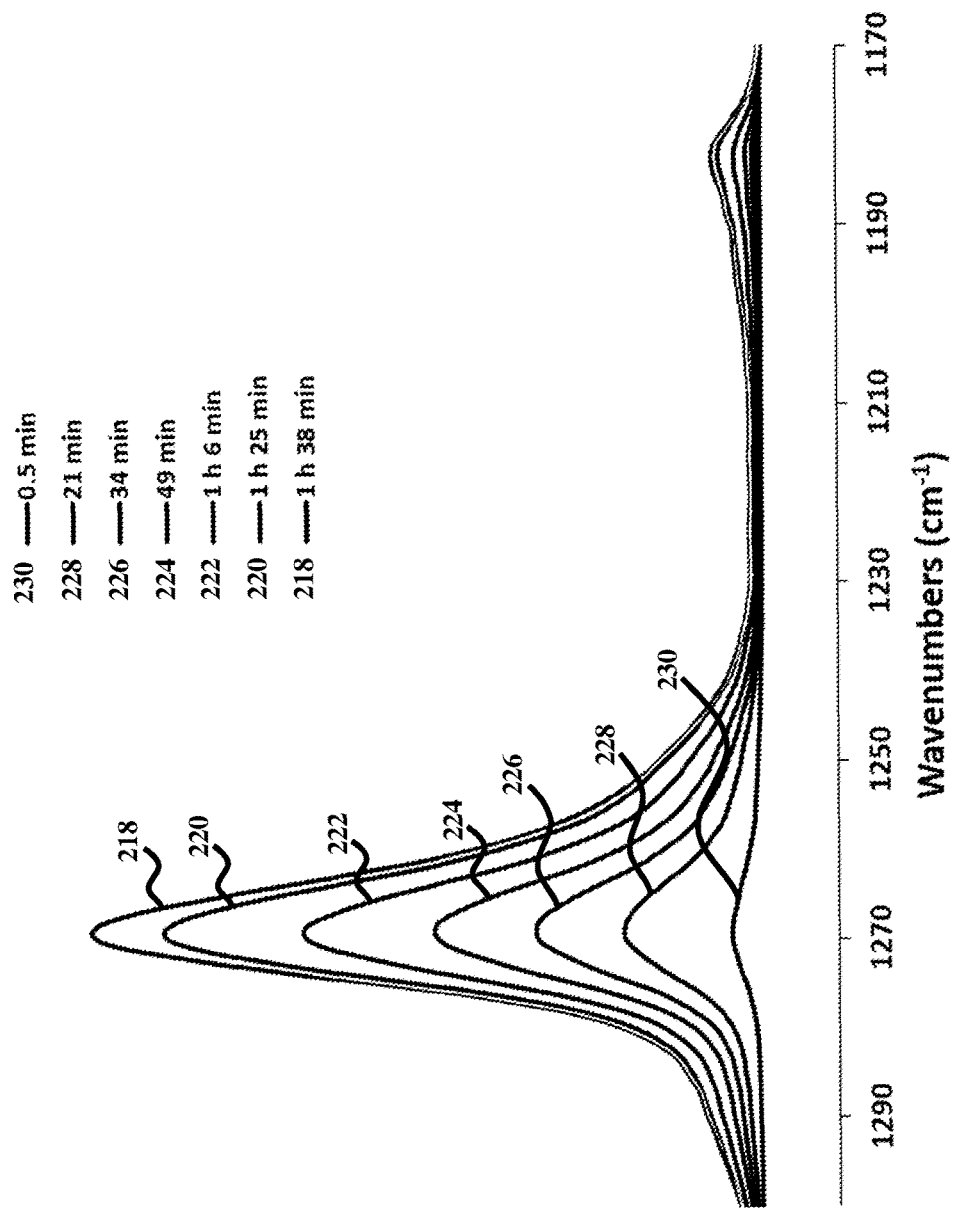
FIG. 3C is a diagram illustrating test results according to an embodiment herein.
Figure 4:
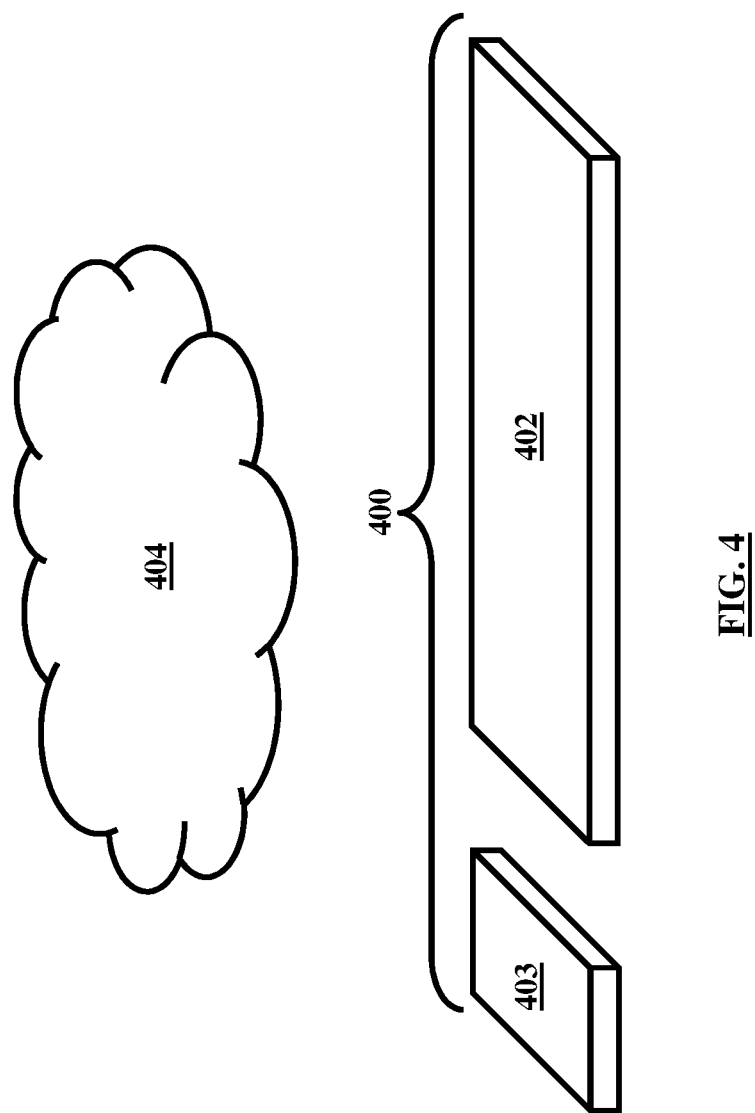
FIG. 4 is a schematic diagram illustrating a composition of matter according to an embodiment herein.
Figure 5:
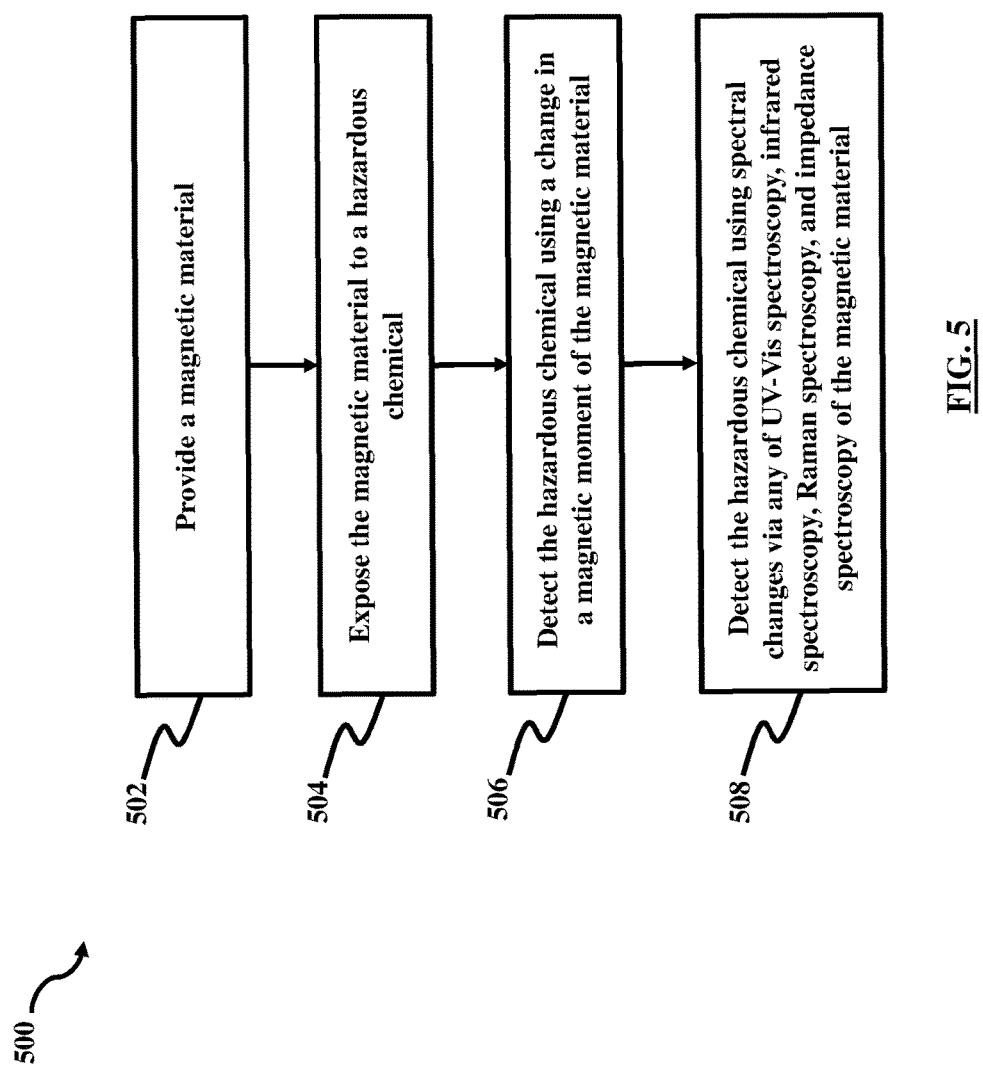
FIG. 5 is a flow diagram illustrating a method according to an embodiment herein.

FIG. 3C, with reference to FIGS. 1A through 3B, is a diagram illustrating test results of IR spectra from device 300, according to an embodiment herein. In-situ IR spectra was collected on the magnetic material of interest 302, which in this case is $Fe_2O_3$ 102. As shown in FIG. 3C, the vibrational (P=O) peak, i.e. approximately 1267 $cm^{-1}$, increases in peak intensity over time as $Fe_2O_3$ 102 is exposed to DMMP 104; thus correlating to surface adsorption from the analyte of interest 320. 0.5 min (line 230), 21 min (line 228), 34 min (line 226), 49 min (line 224), 1 h 6 min (line 222), 1 h 25 min (line 220), and 1 h 38 min (line 218) are all timed in-situ IR spectra collected from $Fe_2O_3$ 102 as it was exposed to DMMP 104.

Several potential uses for embodiments provided herein include a process for (a) sensing the presence of CWAs, specifically G, V, and H agents, and related analogs and (b) decontaminating CWA structural analogs. Embodiments described herein can be used as hazardous chemical sensors or devices, wearable chemical sensors or devices, and magnetic residual life indicators or end-of-service life indicators. Embodiments described herein can be used with a fielded drone configured to detect presence of the hazardous chemical. Other potential uses can be decontaminant wipes, decontaminating sprayable slurry, and wearable chemical sensor. For use as a chemical sensor or device, the magnetic material could be fabricated on a substrate using various deposition techniques, e.g. spray coating, drop casting, electrospray, sputtering deposition, molecular beam epitaxy, lithography, etc., and used for identification of CWA structural analogs. The magnetic material could also be mixed with a polymer. This could also be a wearable chemical sensor fabricated on fabric materials. For decontamination of CWA structural analogs, the process may involve contacting the contaminated surface with the magnetic material. The presence of CWAs and identification may be confirmed by spectral changes and variance in magnetic moment. The magnetic material could possibly be reused by first removing the bound CWAs and demagnetizing the material. Thereafter, the magnetic material can be re-applied to ascertain the presence of residual CWA structural analogs or used in a new contaminated area; thus, extending the life of the magnetic material for recyclable purposes.

FIG. 4, with reference to FIGS. 1A through 3C, is a schematic diagram illustrating a composition of matter 400, according to an embodiment herein. The composition of matter 400 may include a magnetic material 402 for any of chemisorbing, molecular dissociating, and decomposing a hazardous chemical 404. The magnetic material 402 may change cation valency upon any of chemisorption, molecular dissociation, and decomposition of the hazardous chemical 404. The hazardous chemical 404 may include chemical warfare agent structural analogs or other related chemical threats. In an embodiment the magnetic material 402 may further undergo a change in the magnetic moment, stemming from a change in the cation valency upon any of chemisorption, molecular dissociation, and decomposition of the hazardous chemical 404.

In an embodiment, the magnetic material 402 is $Fe_2O_3$ polymorphs, $LnFe_2O_4$ compounds, or other materials.

In an embodiment the magnetic material 402 comprises a metal salt compound. In an embodiment the metal salt compound comprises a first component comprising any of iron I, iron II, iron III, and iron IV, and second component comprising any of oxide, chloride, sulfide, sulfate, sulfite, fluoride, nitride, nitrate, oxynitride, and oxyfluoride.

In an embodiment the metal salt compound comprises any of iron I hydroxide, iron II hydroxide, iron III hydroxide, and iron IV hydroxide. In an embodiment the metal salt compound comprises lanthanide oxide. In an embodiment the metal and salt compound comprises lanthanide iron oxide. In an embodiment the metal salt compound comprises any of manganese II oxide, manganese III oxide, and manganese IV oxide. In an embodiment the metal salt compound comprises manganese tetraoxide.

In an embodiment, the metal salt compound comprises a first component comprising any of manganese II, manganese III, and manganese IV, and a second component comprising any of oxide, chloride, sulfide, sulfate, sulfite, fluoride, nitride, nitrate, oxynitride, and oxyfluoride. In an embodiment the metal salt compound comprises any of cobalt II oxide, and cobalt III oxide. In an embodiment the metal salt compound comprises cobalt as cation and any of chloride, sulfide, sulfate, sulfite, fluoride, nitride, nitrate, oxynitride, and oxyfluoride as anion. In an embodiment, the metal salt compound comprises any of nickel II oxide, and nickel III oxide. In an embodiment, the metal salt compound comprises any of copper I oxide, and copper II oxide. In an embodiment, the metal salt compound comprises copper 11 hydroxide. In an embodiment, the metal salt compound comprises copper II and any of chloride, sulfide, and nitrate.

In an embodiment, the composition of matter 400 may further include a material 403 that shows change in IR spectra. The change in IR spectra may correlate to the chemisorption, molecular dissociation, and/or decomposition of the hazardous chemical 404. Other techniques may also be used such as UV-Vis spectroscopy, Raman spectroscopy, and impedance spectroscopy, correlating to spectral changes from chemisorption, molecular dissociation, and/or decomposition of the hazardous chemical 404. In an embodiment, the impedance spectroscopy uses an electronic property change in the material 403 based on any of chemisorption, decomposition, and molecular dissociation of the hazardous chemical 404. In the impedance spectroscopy, the change in impedance spectra may result from an electronic property change in the material 403 upon any of chemisorption, decomposition, and molecular dissociation of the hazardous chemical 404.

FIG. 5, with reference to FIGS. 1A through 4, illustrates a flow diagram illustrating a method 500, according to an embodiment herein. At step 502, the method 500 provides a magnetic material. At step 504, the method 500 exposes the magnetic material to a hazardous chemical. At step 506, the method 500 detects the hazardous chemical using a change in a magnetic moment of the magnetic material in accordance with chemical exposure. The change in the magnetic moment may stem from a change in a cation valency of the magnetic material upon any of chemisorption, decomposition, and molecular dissociation with the hazardous chemical. The hazardous chemical may include any of chemical warfare agent, chemical warfare agent related compounds, or toxic industrial chemicals.

At step 508, method 500 may detect the hazardous chemical further by spectral changes via any of UV-Vis spectroscopy, infrared spectroscopy, Raman spectroscopy, and impedance spectroscopy of the magnetic material upon any of chemisorption, decomposition, and molecular dissociation with the hazardous chemical. The hazardous chemical may include any of G, V, and H class agents. In an embodiment, the hazardous chemical may include any of sulfur mustard (HD), VX, VE, VG, VM, VR, tabun (GA), soman (GD), cyclosarin (GF), and sarin (GB).

In an embodiment, the hazardous chemical may include other chemical warfare agent structural analogs, wherein the chemical may include any of 2-chloroethyl ethyl sulfide (2-CEES), 2-chloroethylmethyl sulfide (CEMS), dimethyl methylphosphonate (DMMP), dimethyl chlorophosphate (DMCP), diisopropyl methylphosphonate (DIMP), methyl dichlorophosphate (MDCP), diethyl methanephosphonate, diethyl ethanephosphonate, 2,4-dichlorophenol, triethyl phosphate, and diisopropyl fluorophosphonate (DFP).

In an embodiment, the hazardous chemical may include any of acidic or basic gases and vapors. In an embodiment, the hazardous chemical may include any of ammonia, hydrogen chloride, sulfur dioxide, hydrogen sulfide, and cyanogen chloride.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A composition of matter, comprising:
a magnetic material for any of chemisorbing, molecular dissociating, and decomposing a hazardous chemical,
wherein said magnetic material undergoes a change in magnetic moment upon any of chemisorption, decomposition, and molecular dissociation of said hazardous chemical, and
wherein said change in magnetic moment results from a change in a cation valency upon any of said chemisorption, decomposition, and molecular dissociation of said hazardous chemical.

2. The composition of claim 1, further comprising a magnetic material that shows change in any of IR spectra, UV-Vis spectra, Raman spectra, and impedance spectra, wherein said change correlates to said any of chemisorption, decomposition, and molecular dissociation of said hazardous chemical, and wherein said change in impedance spectra results from an electronic property change in said magnetic material upon said any of chemisorption, decomposition, and molecular dissociation of said hazardous chemical.

3. The composition of claim 1, wherein said magnetic material comprises a $LnFe_2O_4$ compound that performs any of chemisorbing, decomposing, and molecular dissociating said hazardous chemical.

4. The composition of claim 3, wherein said lanthanide (Ln) is selected from the group consisting of Ce, Pr, Nd, Pm, Eu, and Tb.

5. The composition of claim 3, wherein said $LnFe_2O_4$ comprises $TmFe_2O_4$.

* * * * *